United States Patent
Gerold et al.

(10) Patent No.: US 9,480,585 B2
(45) Date of Patent: Nov. 1, 2016

(54) IMPLANT OF LOW RADIAL STRENGTH

(75) Inventors: Bodo Gerold, Zellingen (DE); Claus Harder, Uttenreuth (DE); Bernd Heublein, Hannover (DE); Eva Heublein, legal representative, Hannover (DE); Nora Heublein, legal representative, Hannover (DE); Christoph Heublein, legal representative, Hannover (DE); Heinz Mueller, Erlangen (DE)

(73) Assignee: BIOTRONIK VI PATENT AG, Baar (CH)

( * ) Notice: Subject to any disclaimer, the term of this patent is extended or adjusted under 35 U.S.C. 154(b) by 2405 days.

(21) Appl. No.: 11/222,595

(22) Filed: Sep. 9, 2005

(65) Prior Publication Data

US 2006/0064160 A1 Mar. 23, 2006

(30) Foreign Application Priority Data

Sep. 9, 2004 (DE) .................. 10 2004 044 679

(51) Int. Cl.
*A61F 2/06* (2013.01)
*A61F 2/86* (2013.01)
*A61L 31/02* (2006.01)
(Continued)

(52) U.S. Cl.
CPC .............. *A61F 2/86* (2013.01); *A61L 31/022* (2013.01); *A61F 2/90* (2013.01); *A61F 2/91* (2013.01)

(58) Field of Classification Search
CPC .............. A61F 2/86; A61F 2/90; A61F 2/91; A61L 31/022

USPC ............ 623/1.1, 1.11, 1.12, 1.15, 1.18, 1.19, 623/1.2, 1.22, 1.32, 1.38, 1.42, 1.43, 1.44, 623/1.46
IPC ........................................................ A61F 2/06
See application file for complete search history.

(56) References Cited

U.S. PATENT DOCUMENTS 6,245,103 B1 * 6/2001 Stinson ................. 623/1.22
6,248,128 B1 * 6/2001 Berry et al. ............. 623/1.17
(Continued)

FOREIGN PATENT DOCUMENTS

DE 197 31 021 A1 1/1999
DE 102 53 634 A1 5/2004
(Continued)

OTHER PUBLICATIONS

Heublein et al., "Biocorrosion of magnesium alloys: a new principle in cardiovascular implant technology" Jun. 2003.*
(Continued)

*Primary Examiner* — Julie A Szpira
(74) *Attorney, Agent, or Firm* — Greer, Burns & Crain, Ltd.

(57) ABSTRACT

The invention concerns an endovascular implant comprising a biodegradable material and having a tubular main body which is open at the ends and which is dilatable from an unexpanded condition into an expanded condition. The implant is so designed that when the implant in the expanded condition is subjected to a radially acting compression pressure in the range of between 5 and 30 kPa (0.05-0.3 bar) a cross-sectional area of the implant is reduced to 70% or less of the original cross-sectional area, or an internal volume of the implant is reduced to 70% or less of the original internal volume.

20 Claims, 2 Drawing Sheets

(51) Int. Cl.
    *A61F 2/90*     (2013.01)
    *A61F 2/91*     (2013.01)

(56) References Cited

U.S. PATENT DOCUMENTS

| | | | |
|---|---|---|---|
| 6,663,664 B1* | 12/2003 | Pacetti | 623/1.2 |
| 6,991,647 B2* | 1/2006 | Jadhav | 623/1.2 |
| 2003/0050687 A1 | 3/2003 | Schwade et al. | |
| 2003/0077200 A1 | 4/2003 | Craig et al. | |

FOREIGN PATENT DOCUMENTS

| | | |
|---|---|---|
| DE | 698 21 245 T2 | 11/2004 |
| EP | 0 737 453 A2 | 10/1996 |
| EP | 1 184 008 A1 | 3/2002 |

OTHER PUBLICATIONS

L. Duffy, "Magnesium Alloys—Zirconium Containing Casting Alloys" 2003.*

Kornowski et al., "In-Stent Restenosis: Contributions of Inflammatory Responses and Arterial Injury to Neointimal Hyperplasia," Elsevier Science Inc. (U.S.A.), vol. 31 ( No. 1), p. 224-230, (Oct. 24, 1998).

Schmitz et al., "Experimentelle Uberprufung des Aufweitverhaltens von ballonexpandierbaren Koronarstents," p. 203-204, (1997).

Schmidt et al., "Experimentelle Bestimmung der Qualitatsparameter von ballonexpandierbaren Koronarstents," p. 363-364, (1995).

Schmidt et al., "Intravaskulare Stents-Konstruktionsprinzipien und Aufweitverhalten," p. 400-401, (1996).

* cited by examiner

IMPLANT OF LOW RADIAL STRENGTH

BACKGROUND OF THE INVENTION

The invention concerns an endovascular implant comprising a tubular main body which is open at the ends and which is dilatable from an unexpanded condition into an expanded condition.

The implantation of endovascular support systems has been established for many years in medical technology as one of the most effective therapeutic measures in the treatment of vascular diseases. Thus for example, the introduction of stents in interventional therapy in respect of stable and unstable angina pectoris has resulted in a marked reduction in the rate of re-stenoses and thus better long-term results. The cause of using stent implantation in the above-indicated indication is the higher level of primary lumen gain. Admittedly, the use of stents makes it possible to achieve an optimum vessel cross-section which is primarily necessary for therapy success, but it will be noted that the permanent presence of a foreign body of that kind injects a cascade of microbiological processes which can result in the stent gradually growing shut. A starting point for resolving those problems is therefore that of making the stent from a biodegradable material.

A very wide range of different materials are available to the medical technologist, for implementing biodegradable implants of that kind. Besides numerous polymers which, for better biocompatibility, are frequently of natural origin or are at least based on natural compounds, in very recent times metallic materials are favored, with their mechanical properties which are substantially more advantageous in terms of the implants. In that connection, magnesium-bearing, iron-bearing and tungsten-bearing materials are particularly considered.

The endovascular implants are usually dilated with suitable catheter systems at the location of implantation. In general terms in that respect, a distinction can be drawn between self-expanding implants and implants which are only dilated by inflation of a balloon of the catheter system. Self-expanding implants can be formed for example, from shape memory materials such as Nitinol or they have structure elements, the interaction of which, leads mechanically to the desired expansion of the implant. In the case of balloon dilation, the implants which are crimped onto the balloon of the catheter system are uniformly deformed or expanded by the balloon.

One problem in the dilation of endovascular implants is that, when contact is made with the vessel wall or upon expansion of the vessel, the vessel wall suffers from very minor damage, tears and dissections which admittedly generally heal without problem but which can lead to proliferation phenomena due to the cell growth which is triggered off. That adverse effect is tolerated however, in order to prevent excessive contraction of the blood vessel after dilation, with a concomitant constriction in the vessel cross-section (obstruction). In order to counteract that effect, previous solutions provide, for example, applying coating systems to the implant, which contain pharmaceutical substances or which themselves deploy an effect of that kind. In that respect, the previous systems are essentially designed for the requirements involved in the treatment of greatly constricted or closed blood vessels with atherosclerotic plaque. Pathological tissue changes of that kind require a high level of radial strength for the implant in order to obviate obstruction of the vessel. It is admittedly known that vessel injuries result in an inflammatory response on the part of the tissue and ultimately promote neointimal hyperplasia (R. Kornowski, M. K. Hong, F. O. Tio, O. Bramwell, H. Wu, M. B. Leon, JACC, Vol. 31 (1998), No. 1, 224-230), but hitherto, the disadvantages outlined were tolerated in the absence of alternatives.

U.S. Pat. No. 5,888,201 provides that stents with a moderate degree of stiffness and a relatively low modulus of elasticity would be accessible to a wide range of uses. Described therein is a self-expanding stent structure comprising a biocompatible but non-biodegradable titanium alloy.

Besides the mechanical influences on the vessel wall upon dilation, the permanent presence of the implants of conventional nature also represents a re-stenosis point of attack. Frequently however, permanent presence of the implant is not necessary, from the medical point of view. There are therefore, endeavors to form the implant from a biodegradable material. Biodegradable metal alloys are know in this connection, for example based on magnesium, iron, zinc or tungsten.

SUMMARY OF THE INVENTION

An aspect of the present invention was to provide an endovascular implant which is better adapted to the pathological circumstances of a large number of vascular diseases apart from atherosclerotic plaque.

That aspect is attained by an endovascular implant of a biodegradable material having a tubular main body which is open at the ends and which is dilatable from a non-expanded condition into an expanded condition. The implant is so designed that when the implant in the expanded condition is subjected to a radially acting compression pressure in the range of between 5 and 30 kPa (0.05-0.3 bar)

a cross-sectional area of the implant is reduced to 70% or less of the original cross-sectional area, or an internal volume of the implant is reduced to 70% or less of the original internal volume.

In other words, the endovascular implants according to the invention are distinguished inter alia by a lower level of radial strength than the previously known implants of the general kind in the state of the art. For many indications which hitherto were only treated with conventional implants, the healing process can now be substantially improved by means of the implant according to the invention.

Surprisingly, the applicants found in histological studies that a lower level of radial strength of biodegradable implants is not only tolerable for a large number of pathological vascular changes, but leads to a marked improvement in the healing process. Hitherto, it was just the aspect of mechanically keeping open a stenosed vessel that was the foreground consideration, with one and the same type of stent being used for pathophysiologically quite different lesions. The aim, in regard to the development of conventional biodegradable stents, was therefore always that of achieving the highest possible level of radial strength, with the least possible degree of recoil. Clearly however, a very high level of radial strength for the stent is not advantageous for all lesions, but, by virtue of the high mechanical loading that this entails on the vessel wall and the proliferation of smooth vessel muscle cells that is induced thereby, can even be detrimental. By virtue of the complexity of the vascular changes, a biodegradable implant with a lower level of radial strength appears to be particularly advantageous precisely in the area of vulnerable plaques and also in the treatment of dissections of the vessel wall. In the event of excessive mechanical stressing of vulnerable plaques, a thrombus can be formed in the blood stream due to the issue of lipid particles, and that can be the starting point of acute infarcts. Even with only a low degree of radial strength, the permanent presence of the implant can be the starting point for inflammatory or immunological processes which hinder the healing process. The gradual breakdown of the implant in the body cuts the ground away from under such a negative development.

The term "radial strength" is used to denote an internal resistance on the part of the implant in its expanded condition to radially acting forces which could cause radial compression of the implant. Radial strength can be quantitatively expressed by specifying a collapse pressure. In that respect the implants of the state of the art exhibit a collapse behavior in which compression takes place abruptly, that is to say when the collapse pressure is reached the implant collapses very quickly. In vivo however, that collapse behavior is irrelevant as all current implants are designed to resist the forces which occur in the body. The collapse behavior of the implants of the state of the art, which is governed by the aim of affording the highest possible degree of radial strength is however, not absolutely necessary for the purposes of the present invention or does not inevitably occur in the implants according to the invention. Therefore, for the purposes of clarification, the terms "compression pressure" and "compression behavior" which are intended to give expression to the more flexible behavior in relation to radially acting forces have been introduced. Thus it is possible for example, that the cross-sectional area or the internal volume is a monotonically falling function of the radially applied pressure, wherein the reduction according to the invention in the cross-sectional area or the internal volume, occurs when the compression pressure is reached. In other words, starting from the expanded condition, the cross-sectional area or the internal volume is gradually increasingly reduced with an increasing radially applied pressure, until the compression pressure is reached. It is also possible that the function of the cross-sectional area or the internal volume extends in a monotonically falling configuration only as far as a predeterminable limit pressure or limit diameter or limit cross-section and thereafter flattens out (non-linear pressure-diameter configuration). It is possible in that way to avoid far-reaching closure of the vessel/implant when being subjected to the action of a compression pressure, which remains the same.

The term "compression pressure" in the sense according to the invention is used to denote the experimentally determined pressure value, upon the application of which, the expanded implant which is clamped in a test stand falls below 70% of the expanded (original) internal volume. Alternatively, the compression pressure can be defined as the pressure at which the expanded implant at a predetermined cross-section through the implant falls below 70% of the expanded (original) cross-sectional area. For that purpose—quite similarly to the known procedure for determining the collapse pressure of conventional implants—the implant to be tested is accommodated in the expanded condition by a thin-gauge polyurethane hose (wall thickness 0.075 mm), whose lower end is closed and whose upper end is fitted over a tube which permits atmospheric pressure equalization with the interior of the hose. The implant which is enclosed by the hose is then introduced into a closable test chamber filled with warm water at 37° C. By means of a connected pressure control system, the test chamber is subjected to pressure in between 5 and 10 kPa steps, (between 0.05 and 0.1 bar steps). Deformation of the implant, that is to say, a reduction in the cross-sectional area as a consequence of the applied pressure, is measured by way of a laser measuring head whose measuring beam is directed for example approximately onto the center of the implant. With uniform compression of the implant, a change in internal volume can also be derived directly from the detected change in cross-sectional area. If however, the implant collapses non-uniformly when subjected to pressure over its length, measurement is effected at a plurality of points on the implant (at the same time or in a plurality of test series). With a 2-axis laser scanner, in each pressure stage, it is possible to detect the changes in cross-section at various locations of the implant at the same time over its entire length. The number and position of those measurement points are predetermined by the head of the testing procedure, with the proviso that the process involved in compression of the implant is reproduced as exactly as possible over the length thereof. The measurement values obtained make it possible to quantitatively detect the change in internal volume when the implant is subjected to pressure even in the case of implants which collapse in non-uniform fashion.

For further details in regard to determining the collapse pressure as a measurement in respect of radial strength, attention should be directed to the articles by:

- K.-P. Schmitz, D. Behrend, P. Behrens, W. Schmidt, W. Urbaszek, Experimentelle Überprüfung des Aufweitverhaltens von ballonexpandierbaren Koronarstents als Grundlage für in vitro Untersuchungen, Biomedizinische Technik 42 (1997), 203-204,
- W. Schmidt, D. Behrend, A. Nawroth, K.-P. Schmitz, Experimentelle Bestimmung der Qualitätsparameter von ballonexpandierbaren Koronarstents, Biomedizinische Technik 40 (1995), 363-364, and
- W. Schmidt, D. Behrend, P. Behrens, R. Jung, W. Urbaszek, K.-P. Schmitz, Intravaskuläre Stents—Konstruktionsprinzipien und Aufweitverhalten, Biomedizinische Technik 41 (1996), 400-401 the contents of which are hereby incorporated by reference. The mode of approach described therein can be quite similarly applied to determining the compression pressures in accordance with the invention.

The term "biodegradable material" means in the present case that the material is broken down in vivo and consequently the implant can no longer implement its original medical-technical functionality. The decomposition products do not necessarily have to be completely resorbed by the body or excreted. It is also possible for example for small particles to remain at the location of application. Biodegradation in the sense according to the invention concerns, in particular, hydrolytic, enzymatic and other metabolism-governed decomposition processes in the living organism, which lead to gradual dissolution of at least large parts of the materials used. The term biocorrosion is frequently used synonymously. The term bioresorption additionally includes subsequent resorption of the decomposition products.

In accordance with a particular embodiment of the invention, the implant is formed from a magnesium, iron or tungsten alloy. Magnesium alloys of the type WE, in particular WE43, are particularly preferred. The latter alloys are distinguished by the presence of rare earths and yttrium. The specified materials can be easily processed, they involve low material costs and, by virtue of their intrinsic material properties, they permit the implementation of structural measures to achieve the desired collapse pressure ranges. In addition, a positive physiological effect of the decomposition products on the healing process was established at least for a part of the alloys. It was further found that magnesium stents produced from WE43 do not produce any troublesome magnetic resonance artifacts as is known from medical high-quality steel (316L), and for that reason the perfusible lumen of the stent can be assessed at any time after implantation with MR tomography.

The biodegradable metal alloy comprising the elements magnesium, iron or tungsten may contain the specified elements in a respective proportion of at least 50% by weight, in particular at least 70% by weight and particularly preferably at least 90% by weight in relation to the alloy.

The implants can already exhibit the compression behavior according to the invention in the non-degraded condition, that is to say, prior to implantation and initiation of the corrosive processes. A preferred variant however, provides that the implant of the biodegradable alloy is such that the radial strength, according to the invention, occurs only between 1 and 120 h, in particular between 24 and 72 h, after introduction into an artificial plasma at 37° C. in accordance with EN ISO 10993-15:2000. The test conditions allow conclusions to be drawn about the in vivo behavior of the implant. A decomposition behavior on the part of the implant is, inter alia dependent on the material properties (alloy composition, mode of processing, morphology of the material and so forth), the implant design (volume surface, makeup of the structure elements and so forth) and surface modifications (passivation, coatings of biodegradable polymers, roughness and so forth) and generally has to be determined experimentally.

A further preferred embodiment of the implant according to the invention provides that the implant is formed from a material with a modulus of elasticity of between 10 and 60 GPa, in particular between 40 and 50 GPa.

An advantage of materials with a modulus of elasticity in the specified ranges is that, to achieve a low radial strength according to the invention, a width of the legs which are a component part of the support structure of the implant does not have to be reduced, or has to be reduced only to an extent which is relatively slight in comparison with current materials used in implant technology. A suitably wide leg can be desirable in order to keep down the pressure in relation to surface area between the leg and the vessel wall. An excessively high pressure in relation to surface area can lead to damage to the vessel wall. That property is of significance, in particular, in relation to vulnerable plaque. In addition, greater leg widths facilitate and improve manufacture and the liberation behavior of LDD systems (LDD=local drug delivery) which permit active substance elution out of the surface of a leg, for example by application of the active substance or a coating containing the active substance to the surface of the leg.

Endovascular implants according to the invention are suitable for the intravascular treatment of vulnerable plaque ("plaque sealing") or for covering over a dissection of a vascular vessel. The use of the implants is therefore particularly emphasized in connection with those indications.

In both of the stated indications, use is made, in particular, of the particular advantage of the combination of a low level of radial strength and decomposability, due to the use of a biodegradable material:

the aspect which is in the foreground is not mechanically keeping the vessel open, but stabilization of the vessel wall, which is only temporarily required. In the case of vulnerable plaque, there would be a wish to prevent the risk of rupture due to the lipid, which no longer arises when lipid deposit has regressed. When treating dissections the dissecate is "fixed" to the vessel wall and grows on again there.

both indications only require the temporary action of the implant, for which reason it is precisely a degradable stent that should be used, which preferably also has anti-proliferative properties, as could be demonstrated for example by means of the example of stents comprising the magnesium alloy WE43. Conventional permanent stents are known to have disadvantages in regard to their re-stenosis rate (which is markedly different from zero even in the case of lesions which are hemodynamically less relevant) and also in regard to their prerequisites for possibly subsequently required re-intervention and their diagnostic options, for example governed by MR artefacts.

BRIEF DESCRIPTION OF THE SEVERAL VIEWS OF THE DRAWINGS

The invention is described in greater detail hereinafter by means of embodiments by way of example and with reference to the accompanying drawings in which.

DETAILED DESCRIPTION OF THE INVENTION

Embodiment 1

Figure 1:
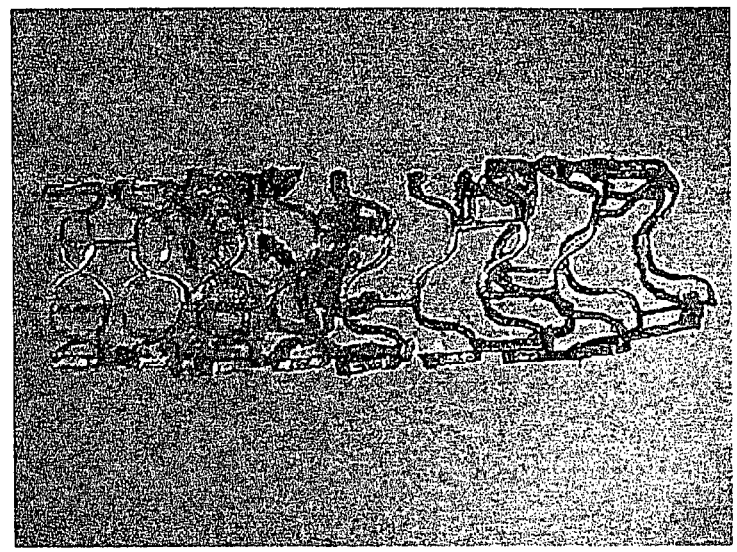
FIG. 1 is a photographic reproduction of a stent after storage in artificial plasma for 48 h.

Sterilized stents comprising the in vivo degradable magnesium alloy WE43 were investigated. The stents were serially numbered for the investigations (Nos 1-14). The stents were of a diameter of 3.0 mm and stents Nos. 1, 3 and 5 were of a length of 15 mm while stents Nos. 2, 4 and 6 through 14 were of a length of 10 mm.

The radial strength of the degradable stents was investigated after storage in a corrosive environment. For that purpose, after a defined storage time, the compression pressure was measured as a measurement in respect of radial strength.

Before being put into storage in the test medium, the test objects which are in the form of bare stents were implanted into sterilized polyurethane hoses (inside diameter 3 mm, wall gauge 0.075 mm, sterilization with formaldehyde vapor (FAD) with an inwardly disposed distal sleeve (Teflon). Implantation was effected manually under sterile laminar flow conditions.

Firstly the stent was removed from the specimen container and crimped manually onto a sterile balloon catheter (Biotronik Lekton Motion). The stent was now expanded in the PU hose with a nominal pressure 600 kPa (6 bars). That caused the PU hose to be over-stretched, which resulted in a static loading on the stent as a consequence of the wall stresses in the PU hose. With the test hose diameter used, of an inside diameter of 3.0 mm and a wall gauge of 0.075 mm, overstretching of 0.050 mm resulted in an additional static loading of 23 kPa (0.23 bar). The balloon catheter was then removed again. A balloon catheter was used for three stent expansion operations.

The test hose was filled with test medium using a disposable syringe and cannula and then stored in 50 ml of test medium so that the stents were in complete contact with the test medium during the storage operation. A sterile, artificial plasma, as is provided in accordance with EN ISO 10993-15:2000 for degradation investigations was used as the test medium, of the following composition:

NaCl, 6.800 g/l;
$CaCl_2$, 0.200 g/l;
KCl, 0.400 g/l;
$MgSO_4$, 0.100 g/l;
$NaHCO_3$, 2.200 g/l;
$Na_2HPO_4$, 0.126 g/l;
$NaH_2PO_4$, 0.026 g/l.

A total of eleven closed specimen containers each with 50 ml of test medium and a respective PU hose with an Mg stent were then stored in a breeding cabinet at 37° C.

The total of 14 investigated Mg stents were investigated in five groups. In that case the first group with 3 stents (Nos 10, 11 and 12) served as a reference (without test medium contact). 3 stents were respectively removed from the test medium after 24, 48 and 72 h, and 2 stents after 120 h, and radial strength was measured.

Figure 2:
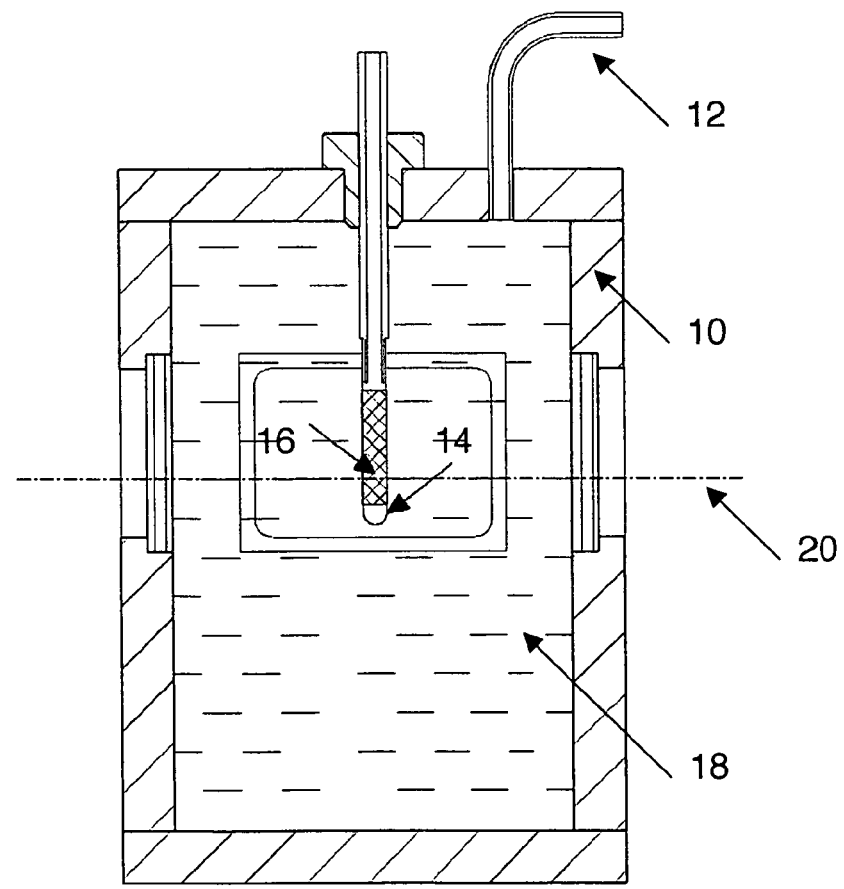
FIG. 2 shows a chamber for testing radial strength.

For the purposes of measuring radial strength the stent 16 disposed in a thin-gauge PUR hose 14 (inside diameter 3.0 mm, wall thickness 0.075 mm) was stored in a test vessel 10 filled with water (37° C.) (FIG. 2). The test medium was pipetted out of the PUR hose 14.

The test vessel 10 was pressure-tightly closed and connected to a pressure control system 12 (BALTUS). The pressure in the vessel 18 was increased stepwise in 5 kPa steps (0.05 bar steps) to a maximum of 150 kPa (1.5 bar) and by way of the PUR hose 14 applied a radial loading to the stent 16. In that situation, the change in diameter was measured at the stent center, in dependence on the ambient pressure, by means of a laser 20. The compression pressure at which the cross-sectional area of the stent 16 is reduced to 70% or less of the original cross-sectional area was noted.

The measured compression pressure values are entered in Table I for the stents investigated, in dependence on the storage time. FIG. 1 shows, by way of example, stent No. 8 after removal from the artificial plasma.

TABLE I

Table 1: Measurement results (1 bar = 100 kPa)

| Storage time [h] | Stent (Number) | Compression pressure [bar]* | Mean compression pressure [bar]* |
|---|---|---|---|
| 0 | (10) | 1.05 | 0.85 |
|   | (11) | 0.85 |   |
|   | (12) | 0.65 |   |
| 24 | (2) | 0.70 | 0.60 |
|   | (4) | 0.55 |   |
|   | (6) | 0.55 |   |
| 48 | (7) | 0.30 | 0.38 |
|   | (8) | 0.45 |   |
|   | (9) | 0.40 |   |
| 72 | (1) | 0.45 | 0.30 |
|   | (3) | 0.15 |   |
|   | (5) | 0.30 |   |
| 120 | (13) | 0.25 | 0.225 |
|   | (14) | 0.20 |   |

Embodiment 2

Figure 3:
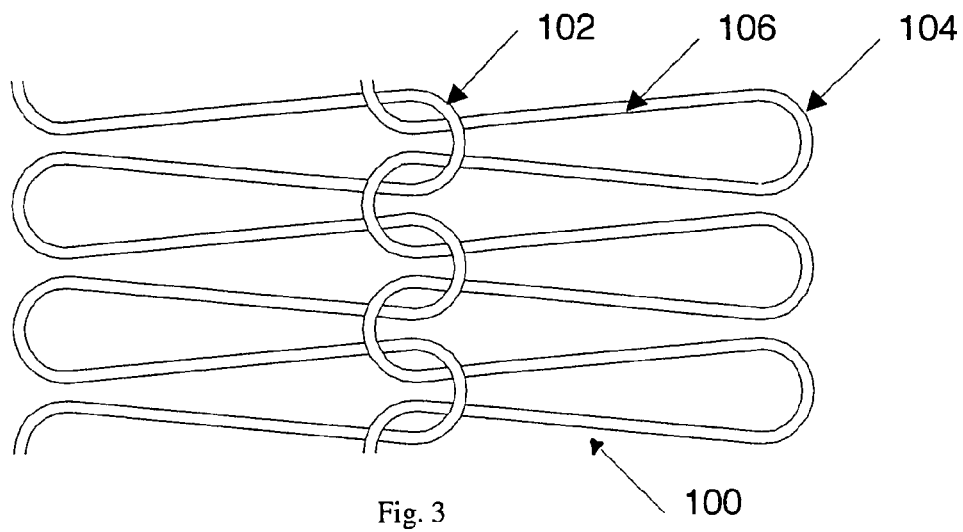
FIG. 3 shows a further design for a stent with the radial strength according to the invention.

FIG. 3 shows a portion from a development of a stent illustrating a balloon-expandable structure 100 on a wire basis, which is composed of a multiplicity of individual ring segments. No transverse forces are transmitted by the flexible connection 102 of the individual ring segments, even in the case of curved vessels. The bending radius 104 is adapted to the material properties and the desired maximum opening diameter. The length of the element 106, together with the wire diameter, determines the radial strength. In particular the biodegradable magnesium alloy WE43 is suitable as the material.

Embodiment 3

Figure 4:
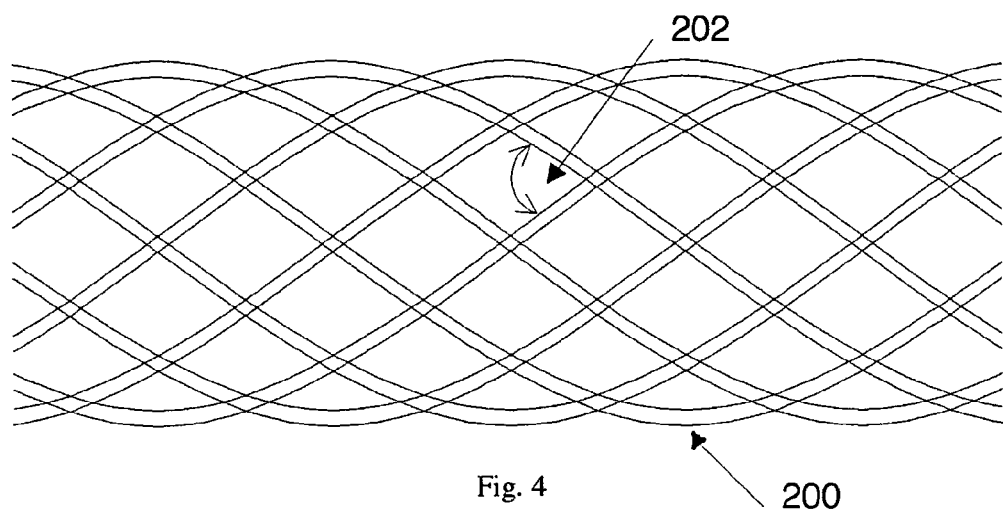
FIG. 4 shows a further design for a stent with the radial strength according to the invention.

FIG. 4 shows a self-expandable structure 200 on a wire basis.

Described hereinafter are various measures in terms of the stent design, by means of which the radial strength can be set to the range of values according to the invention. The measures are based on established theoretical considerations and are familiar to the individual skilled in the art per se so that the practical implementation thereof can be effected at a low level of experimental complication and expenditure. The measures are to be respectively matched to each other, so as to give a radial strength in the desired value range.

A first measure provides that a biodegradable material with a low modulus of elasticity is used. By way of example, the magnesium alloy WE43 with a modulus of elasticity of approximately 45,000 MPa presents itself as being suitable. If the illustrated structure is wound from twenty wires of a wire diameter of 0.09 mm, at an angle 202 of 110°, to form a stent of diameter of 5 mm, an investigation by way of example, shows that a radial strength of approximately 5 kPa (0.05 bar) is to be expected. That investigation is discussed in greater detail in U.S. Pat. No. 5,888,201 to Stinson et al., the disclosure of which is incorporated by reference herein. In that respect, the influence of friction between the stent and the vessel wall is not taken into consideration. One of the typical properties of this embodiment is the relatively great change in length with a change in diameter of preferably 70% of the nominal diameter. If the change in length is hindered by wall friction, the change in diameter is also hindered, which leads to an increased radial strength. Theoretical considerations show that the effect can be reduced by a reduction in the angle 202. Accordingly, adjustment of the desired level of radial strength can also be achieved by altering the angle 202. Theoretical considerations which take account of all those circumstances show that the radial strength of a stent of a material and of dimensions as described above, after implantation, will increase from the calculated 5 kPa (0.05 bar) to about 20 kPa (0.2 bar). If experiments (for example measurement of the collapse pressure using the above-described method) should show that the desired level of radial strength of for example 20 kPa (0.2 bar) is not reached, then preferably the wire diameter would have to be increased from 0.09 mm as described above, to for example, 0.1 mm. If the measured radial strength should be too high, then theoretical considerations show that a reduction in the wire diameter or also a reduction in the angle 202 to for example 90°, instead of the above-mentioned 110°, also leads to a reduction in the radial strength. In that case, preferably the angle 202 should be reduced as the reduction in angle also provides that a reduced change in length occurs and thus the dependency of the radial strength on wall friction is reduced. Theoretical considerations lead to an expectation of a high degree of variability in wall friction depending on the respective stenosis type, in accordance with the foregoing considerations, accordingly a high level of variability in radial strength would also be expected with this embodiment. The variability in radial strength can be reduced by a reduction in the angle 202.

A further measure for reducing radial strength can be achieved by a reduction in the number of interwoven wires. The number of interwoven wires is limited downwardly as, with an excessively small number of wires, the free ends could be undesirably formed outwardly or inwardly. These correlations are described in U.S. Pat. No. 5,061,275 to Wallsten et al., the disclosure of which is hereby incorporated by reference herein.

Embodiment 4

Figure 5:
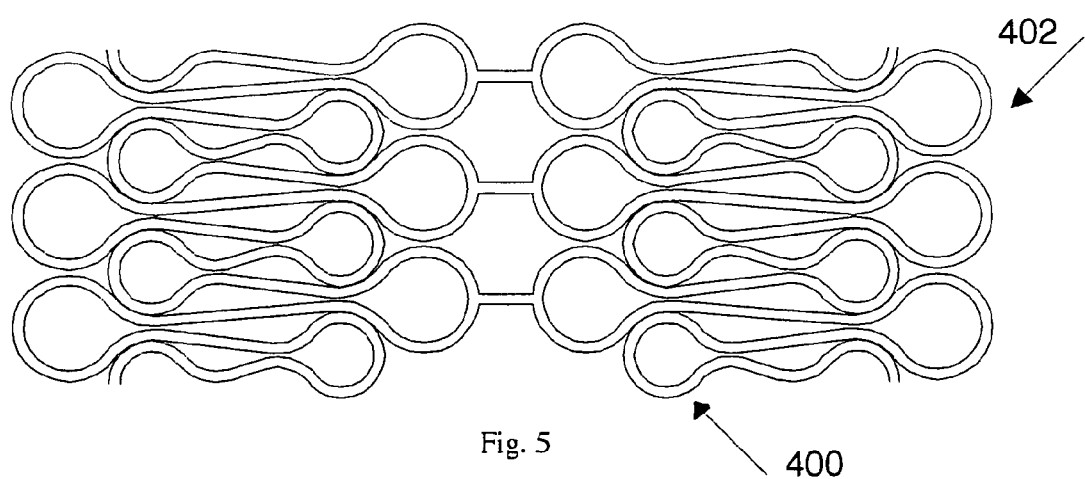
FIG. 5 shows a further design for a stent with the radial strength according to the invention.

FIG. 5 shows a self-expandable structure 400 (here in the closed condition) which is cut from a magnesium tube of the alloy WE43 of a nominal diameter of 8 mm. Due to the large radii 402, the slight stretch capability of the magnesium alloy is not exceeded and at the same time the desired radial strength is predetermined.

We claim:

1. An endovascular implant comprising a biodegradable material and having a tubular main body which is open at the ends and which is dilatable from an unexpanded condition into an expanded condition, wherein the implant is so designed that, prior to implantation, when the implant in the expanded condition is subjected to a radially acting compression pressure in the range of between 5 and 30 kPa (0.05-0.3 bar)
   a cross-sectional area of the implant is reduced to 70% or less of the original cross-sectional area, or
   an internal volume of the implant is reduced to 70% or less of the original internal volume.

2. An implant as set forth in claim 1, wherein the compression pressure is in the range of between 10 and 20 kPa (between 0.1 and 0.2 bar).

3. An implant as set forth in claim 1, wherein the implant is formed from a material with a modulus of elasticity of between 10 and 60 GPa.

4. An implant as set forth in claim 3, wherein the implant is formed from a material with a modulus of elasticity of between 40 and 50 GPa.

5. An implant as set forth in claim 1, wherein the biodegradable material is a biodegradable magnesium, iron or tungsten alloy.

6. An implant as set forth in claim 5, wherein the magnesium alloy is an alloy of type WE.

7. An implant as set forth in claim 6, wherein the alloy is of type WE43.

8. An implant as set forth in claim 7, wherein the implant of a biodegradable alloy is of such a nature that a desired radial strength only occurs at between 1 and 120 h after introduction into 37° C. artificial plasma in accordance with EN ISO 10993-15:2000.

9. An implant as set forth in claim 8, wherein a desired radial strength occurs between 24 and 72 h after introduction into 37° C. artificial plasma in accordance with EN ISO 10993-15:2000.

10. An implant as set forth in claim 2, wherein the biodegradable material is a biodegradable magnesium, iron or tungsten alloy.

11. An implant as set forth in claim 3 wherein the biodegradable material is a biodegradable magnesium, iron or tungsten alloy.

12. An implant as set forth in claim 4, wherein the biodegradable material is a biodegradable magnesium, iron or tungsten alloy.

13. An implant as set forth in claim 10, wherein the magnesium alloy is an alloy of type WE.

14. An implant as set forth in claim 11, wherein the magnesium alloy is an alloy of type WE.

15. An implant as set forth in claim 12, wherein the magnesium alloy is an alloy of type WE.

16. An implant as set forth in claim 13, wherein the alloy is of type WE43.

17. An implant as set forth in claim 14, wherein the alloy is of type WE43.

18. An implant as set forth in claim 16, wherein the implant of a biodegradable alloy is of such a nature that a desired radial strength only occurs at between 1 and 120 h after introduction into 37° C. artificial plasma in accordance with EN ISO 10993-15:2000.

19. An implant as set forth in claim 15, wherein the implant of a biodegradable alloy is of such a nature that a desired radial strength only occurs at between 1 and 120 h after introduction into 37° C. artificial plasma in accordance with EN ISO 10993-15:2000.

20. A method of treating a patient, the method comprising inserting an endovascular implant into the patient, wherein the implant comprises a biodegradable material having a tubular main body which is open at the ends, wherein the implant is adapted to be dilatable from an unexpanded condition to an expanded condition, and wherein, the implant is adapted such that, prior to implantation, when the implant in the expanded condition is subjected to a radially acting compression pressure between about 5 and about 30 kPa (about 0.05-0.3 bar), the cross-sectional area of the implant is reduced to 70 percent or less of the original cross-sectional area or an internal volume of the implant is reduced to 70 percent or less of the original internal volume.

* * * * *